United States Patent
Wong et al.

[11] Patent Number: 6,077,660
[45] Date of Patent: *Jun. 20, 2000

[54] DIAGNOSTIC ASSAY REQUIRING A SMALL SAMPLE OF BIOLOGICAL FLUID

[75] Inventors: Sie Ting Wong, Mundelein, Ill.; Robert G. Hiltibran, Bristol, Wis.; Tung-Ming Huang, Buffalo Grove, Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/095,683

[22] Filed: Jun. 10, 1998

[51] Int. Cl.[7] .............................. C12Q 1/00; C12Q 1/32; C12Q 1/54; A01N 1/02
[52] U.S. Cl. .................................. 435/4; 435/26; 435/14; 435/283.1; 435/289.1; 422/50; 422/55
[58] Field of Search .................................. 435/4, 26, 14, 435/283.1, 289.1; 422/50, 55

[56] References Cited

U.S. PATENT DOCUMENTS

| | | | |
|---|---|---|---|
| 4,088,448 | 5/1978 | Lija et al. ..................................... | 435/4 |
| 4,243,753 | 1/1981 | Regnier et al. .............................. | 435/4 |
| 4,276,051 | 6/1981 | Ginsberg et al. ............................ | 435/4 |
| 4,297,238 | 10/1981 | Vormbrock et al. ........................ | 435/4 |
| 4,540,670 | 9/1985 | Arai et al. ................................... | 435/4 |
| 4,594,327 | 6/1986 | Zuk .............................................. | 435/4 |
| 4,708,933 | 11/1987 | Huang et al. ................................ | 435/4 |
| 4,711,245 | 12/1987 | Higgins et al. .............................. | 435/4 |
| 4,772,561 | 9/1988 | Genshaw ..................................... | 435/4 |
| 4,775,361 | 10/1988 | Jacques et al. .............................. | 435/4 |
| 4,920,056 | 4/1990 | Dasgupta ..................................... | 435/4 |
| 5,000,922 | 3/1991 | Turpen ......................................... | 435/4 |
| 5,037,737 | 8/1991 | Liffmann et al. ............................ | 435/4 |
| 5,147,606 | 9/1992 | Charlton et al. . | |
| 5,161,532 | 11/1992 | Joseph ......................................... | 435/4 |
| 5,202,261 | 4/1993 | Musho et al. ................................ | 435/4 |
| 5,250,439 | 10/1993 | Musho et al. ................................ | 435/4 |
| 5,278,047 | 1/1994 | Lilja et al. . | |
| 5,384,093 | 1/1995 | Ootani et al. ................................ | 435/4 |
| 5,423,803 | 6/1995 | Tankovich et al. .......................... | 435/4 |
| 5,480,614 | 1/1996 | Kamahori .................................... | 435/4 |
| 5,486,478 | 1/1996 | Kuriyama .................................... | 435/4 |
| 5,508,200 | 4/1996 | Tiffany et al. ............................... | 435/4 |
| 5,538,857 | 7/1996 | Rosenthal et al. ........................... | 435/4 |
| 5,607,565 | 3/1997 | Azarnia et al. .............................. | 435/4 |
| 5,843,691 | 12/1998 | Douglas et al. ............................. | 435/4 |

FOREIGN PATENT DOCUMENTS

| | | |
|---|---|---|
| 9409713 | 5/1994 | WIPO . |
| 9707734 | 3/1997 | WIPO . |

*Primary Examiner*—Louise N. Leary
*Attorney, Agent, or Firm*—David L. Weinstein

[57] ABSTRACT

An article and a method for monitoring the concentration of glucose in blood. In one aspect, the invention involves an article comprising a multiple-layer element utilizing reagents capable of reacting with an analyte of interest. In a preferred embodiment, the element comprises:

(a) a core layer having two major surfaces, an optical reading chamber extending from a first opening in one of the two major surfaces to a second opening in the other of the two major surfaces, the core layer further having a third opening therein and a flow channel, one end of which flow channel communicates with the third opening and the other end of which flow channel communicates with the optical reading chamber;

(b) a base layer in face-to-face contact with one major surface of the core layer; and (c) a cover layer in face-to-face contact with the other major surface of the core layer, the cover layer having an opening therein to vent the element.

In another aspect, the invention involves a method comprising the steps of:

(a) obtaining a sample of biological fluid, e.g., interstitial fluid, from the body of a patient;

(b) introducing the sample to an article comprising a multiple-layer element having an optical reading chamber;

(c) allowing reagents to react with an analyte of interest in the sample; and (d) measuring the concentration of analyte in the sample by means of an optical instrument.

34 Claims, 11 Drawing Sheets

DIAGNOSTIC ASSAY REQUIRING A SMALL SAMPLE OF BIOLOGICAL FLUID

BACKGROUND OF THE INVENTION

1. Field of the Invention

This invention relates to the field of monitoring the amount of analyte, e.g., glucose, cholesterol, in body fluid. More particularly, this invention provides an article and method that monitors the amount of analyte in body fluid by means of a test that employs only a small volume of biological fluid.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

There are numerous devices currently available for diabetics to monitor the level of blood glucose. The best of these devices require the diabetic to prick a finger and to collect a drop of blood for placement on a strip, which is inserted into a monitor that determines the level of glucose in the blood. Pricking one's finger tends to be painful. Moreover, a relatively large wound is produced by the pricking device, typically a lancet or a needle. It is known that the pain arising from the finger prick deters diabetics from compliance with the monitoring regimen. Lack of compliance increases the risk of complications due to diabetes. Thus there is a need for a more painless and less traumatic means of collecting biological samples for monitoring one's level of glucose in blood.

Several patents have proposed that the level of glucose in blood can be monitored by measuring the level of glucose in interstitial fluid. In order to obtain samples of interstitial fluid, the barrier function of the stratum corneum must be overcome. Jacques, U.S. Pat. No. 4,775,361, discloses a method of ablating the stratum corneum of a region of the skin of a patient by using pulsed laser light of a wavelength, pulse length, pulse energy, pulse number, and pulse repetition rate sufficient to ablate the stratum corneum without significantly damaging the underlying epidermis. This patent discloses the use of laser light having a wavelength of 193 nm or 2940 nm. Laser light having wavelengths of 193 nm or 2940 nm can be provided by an excimer or Er:YAG light source, respectively, both of which are extremely expensive.

Tankovich, U.S. Pat. No. 5,423,803, discloses a process for the removal of superficial epidermal skin cells in the human skin. A contaminant having a high absorption in at least one wavelength of light is topically applied to the surface of the skin. Some of the contaminant is forced to infiltrate into spaces between superficial epidermal cells. The skin section is illuminated with short laser pulses, with at least at least one of the pulses having sufficient energy to cause some of the particles to explode tearing off the superficial epidermal cells.

Zahrov, WO 94/09713, discloses a method for perforating skin comprising the steps of (a) focusing a laser beam in the shape of an ellipse at the surface of the skin with sufficient energy density to create a hole at least as deep as the keratin layer and at most as deep as the capillary layer; and (b) creating at least one hole, each hole having a width between 0.05 and 0.5 mm and a length of equal to or less than 2.5 mm.

It should be noted that it is desirable for a diagnostic device for monitoring glucose provide a result rapidly. Most commercially available devices provide a result in under one minute. This one-minute period runs from the moment of sticking the finger to the display of the result on a meter. When interstitial fluid is used as the sample, the goal of a one-minute testing period is difficult to satisfy, because the methods for obtaining interstitial fluid typically provide samples of less than 1 $\mu$L per minute. In order to determine the quantity of glucose in a sample of interstitial fluid, sensitive detection methods must be employed. It is well known that a common method for increasing assay sensitivity is to increase the size of the biological sample. However, increasing the size of a sample of some biological fluids, such as interstitial fluid, has been found to be difficult.

U.S. Pat. Nos. 5,161,532; 5,508,200; 5,202,261 disclose the use of biological fluids to determine the concentration of glucose in the blood. U.S. Pat. No. 5,161,532 discloses an interstitial fluid sensor. The sensor is applied to the skin of a person or animal to detect the chemical components of the interstitial fluid. The sensor comprises a substrate of porous material, which permits the passage of the interstitial fluid therethrough. At least two electrodes are provided. One of the electrodes has two sides, with one side mounted on the substrate. The one electrode is also of a porous material for the passage of the interstitial fluid from the one side in contact with the substrate to through to the second side, which is generally opposite the one side. A layer of chemical is on the second side. The layer comprises a chemical for reaction with one component in the interstitial fluid. The chemical is mixed in a mediating agent. The electrodes produce a response to the reaction of one component of the interstitial fluid with the chemical. A detector receives the electrical signal; generated by the electrodes and generates a display indicative of the amount of the one component in the interstitial fluid. According to this patent, at a sampling rate of approximately 0.4 microliter/min/cm$^2$, the entire electrodes can be wetted in less than 2 seconds.

U.S. Pat. No. 5,508,200 discloses a system for high performance automated chemical analysis including a video camera photometer with a computer-controlled interference filter wheel. A fluidics system delivers ultramicro sample and reagent volumes in the 0.05 to 5.0 microliter range to a supporting analytical media. The media is precisely positioned relative to the photometer by an x-y axis reaction media holder capable of accurate and precise position of the ultramicro reaction spots. The reaction media can consist of absorbent cellulose sample/reaction strips or microscopic sized multiple wells. A data and reduction system monitors multiple simultaneous reactions within a common test area of the analytical media to provide final quantitative reports. The method for conducting multiple chemical assays involves placing small volumes of sample/reagent combinations at discrete locations about a common test area on the analytical media and simultaneously measuring resulting optical changes at each discrete location.

U.S. Pat. No. 5,202,261 discloses a diagnostic device including a conductive analyte sensor comprising a reaction zone and a detection zone, wherein the detection zone includes a conducting polymer and a microelectrode assembly. The conductive sensor allows the detection and measurement of a predetermined analyte in a liquid test sample, wherein the predetermined analyte is assayed by an oxidase interaction. An interaction between the predetermined analyte and an oxidase enzyme occurs in the reaction zone of the conductive sensor to produce, either directly or indirectly, a dopant compound that migrates to the detection zone of the sensor. The detection zone of the device is in laminar contact with the reaction zone and includes a layer or film of conducting polymer that is oxidized by the dopant compound. Therefore, the conductivity of the conducting polymer is changed, and the change in conductivity of the conducting polymer layer is detected and measured by the microelectrode assembly and is correlated to the concentration of predetermined analyte in the sample. The device can utilize a test sample having a volume of from about 0.1 $\mu$L to about 5 $\mu$L, and usually less than 1 $\mu$L of whole blood.

It would be desirable to provide a means for detecting the concentration of glucose in small volumes of interstitial fluid, preferably with an optical reading system, because such a system is more sensitive than an electrochemical reading system.

SUMMARY OF THE INVENTION

This invention provides an article and a method for monitoring the concentration of glucose in blood. In one aspect, the invention involves an article comprising a multiple-layer element utilizing reagents capable of reacting with an analyte of interest. In one embodiment, the element comprises:

(a) a base layer having two major surfaces, the base layer further having an opening, a flow channel, and an optical reading chamber, one end of which flow channel communicates with the opening in the base layer and the other end of which flow channel communicates with the optical reading chamber; and (b) a cover layer in face-to-face contact with the major surface of the base layer containing the opening, the cover layer having an opening therein to vent the element.

In this embodiment, the optical reading chamber does not extend completely through the base layer. The sample is introduced into the opening in the base layer and then flows through the flow channel into the optical reading chamber. The reagents with which the analyte in the sample reacts to form an optically detectable reaction product can be disposed in the optical reading chamber or can be added to the sample before the sample enters the optical reading chamber.

In a preferred embodiment, the element comprises:

(a) a core layer having two major surfaces, the core layer further having an opening, a flow channel, and an optical reading chamber, one end of which flow channel communicates with the opening in the core layer and the other end of which flow channel communicates with the optical reading chamber; and (b) a base layer in face-to-face contact with one major surface of the core layer; and (c) a cover layer in face-to-face contact with the other major surface of the core layer, said cover layer having an opening therein to vent the element.

In this embodiment, the optical reading chamber extends completely through the core layer. The sample is introduced into the opening in the core layer and then flows through the flow channel into the optical reading chamber. The reagents with which the analyte in the sample reacts to form an optically detectable reaction product can be disposed in the optical reading chamber or can be added to the sample before the sample enters the optical reading chamber.

In another aspect, the invention involves a method comprising the steps of:

(a) obtaining a sample of biological fluid, e.g., interstitial fluid, from the body of a patient;

(b) introducing the sample to article comprising a multiple-layer element having an optical reading chamber;

(c) allowing reagents to react with an analyte of interest in the sample; and (d) measuring the concentration of analyte in the sample by means of an optical instrument.

The reagents can be made to react with the sample in one of a number of ways. It is preferred that the reagents be deposited in the optical reading chamber of the multiple-layer element. Alternatively, the reagents can be mixed with the sample, and the resulting reaction mixture can be introduced to the multiple-layer element. As another alternative, a liquid reagent can be introduced to the multiple-layer element and then the sample can be introduced to the multiple-layer element.

The article and process of this invention allow the use of samples of extremely low volume to provide extremely sensitive assay results. The article and process of this invention do not require the use of complicated delivery equipment, e.g., precision pipettes. The article of this invention is self-filling and can be filled with a precise amount of sample.

The article has been shown to provide accurate and reproducible results with samples having a volume of as low as about 0.25 $\mu$L.

DETAILED DESCRIPTION

This invention provides an article and a method for monitoring the concentration of an analyte, e.g., glucose, in blood. In one aspect, the invention involves an article comprising a multiple-layer element utilizing reagents capable of reacting with an analyte of interest. In another aspect, the invention involves a method for monitoring the concentration of an analyte in blood by using the article.

Figure 1:
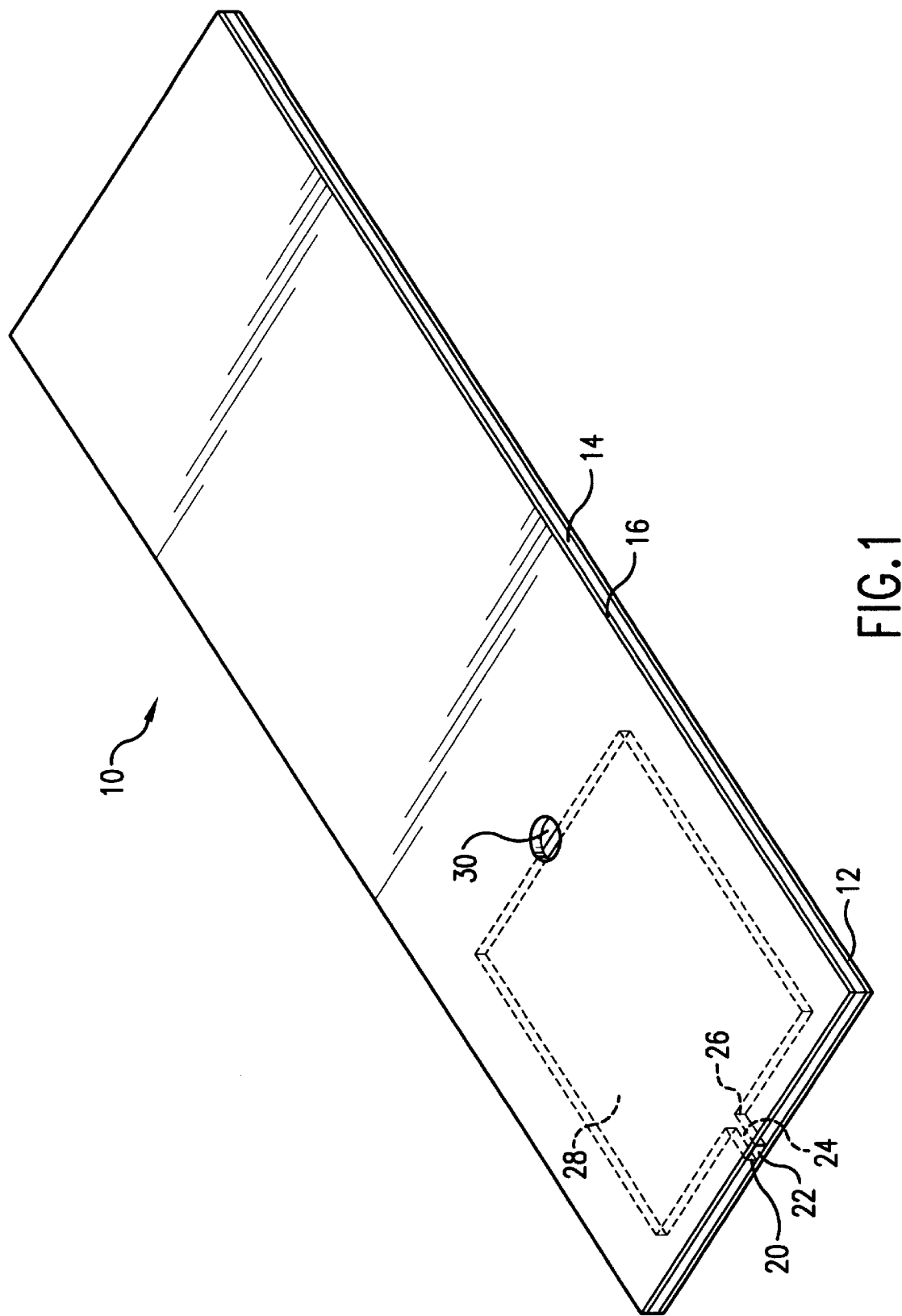
FIG. 1 is a perspective view of an embodiment of an article suitable for use in this invention.
Figure 2:
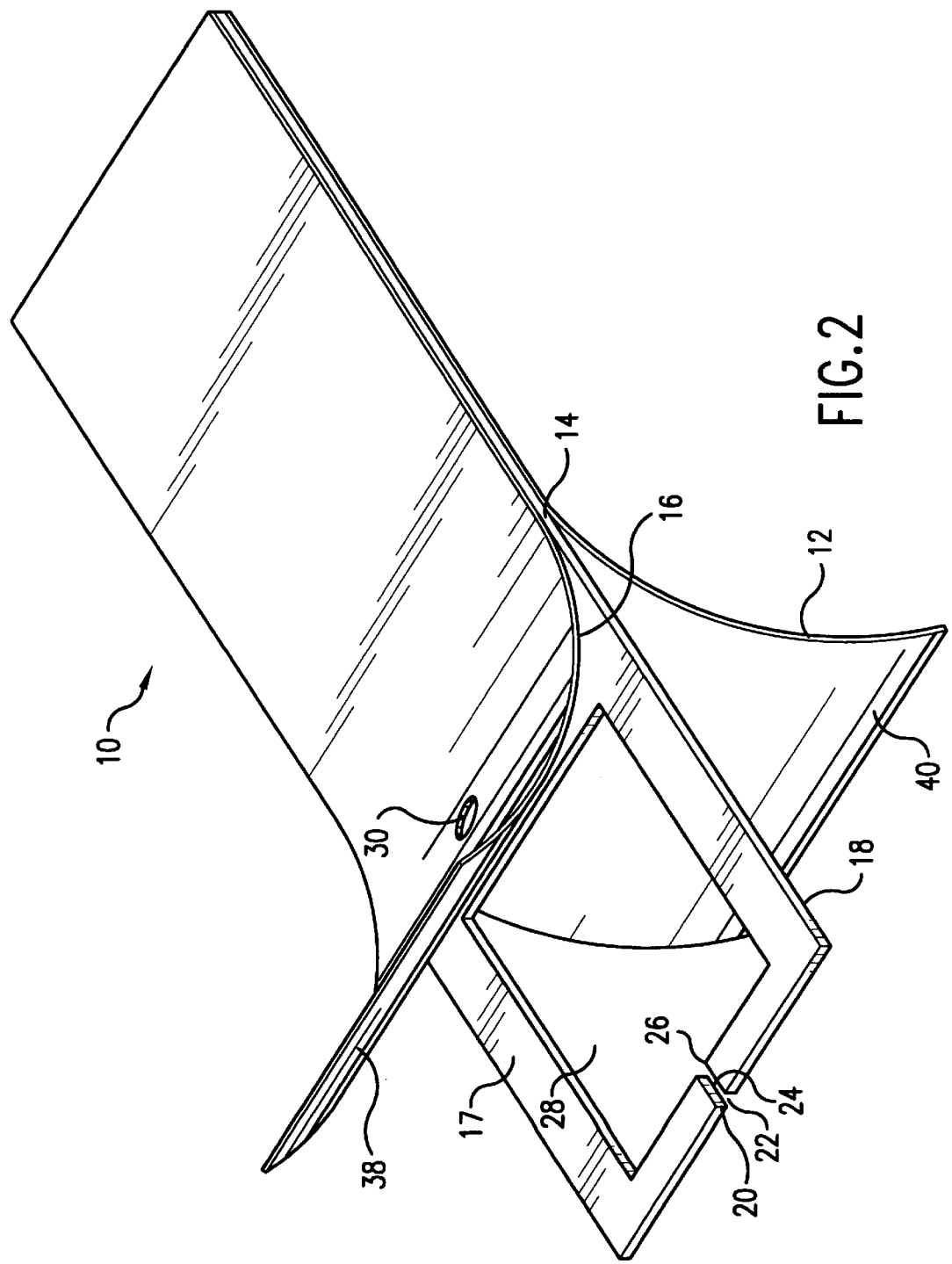
FIG. 2 is a perspective view of the embodiment shown in FIG. 1, with the layers shown peeled-apart.
Figure 3:
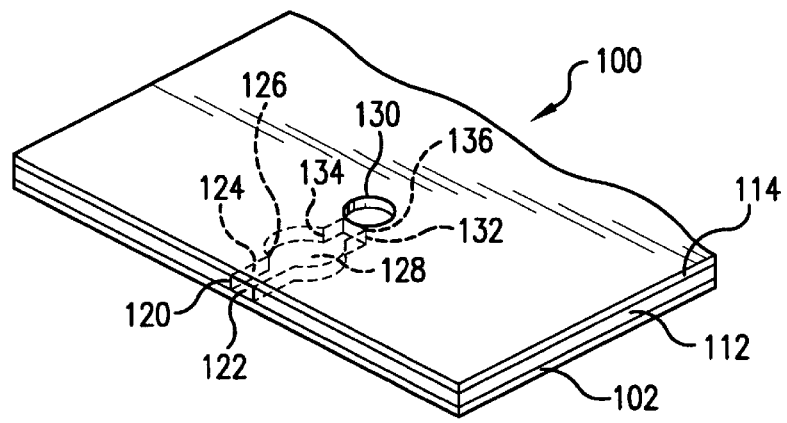
FIG. 3 is a partial perspective view of a preferred embodiment of an article suitable for use in this invention. The view illustrates the functional portion of the article.
Figure 4:
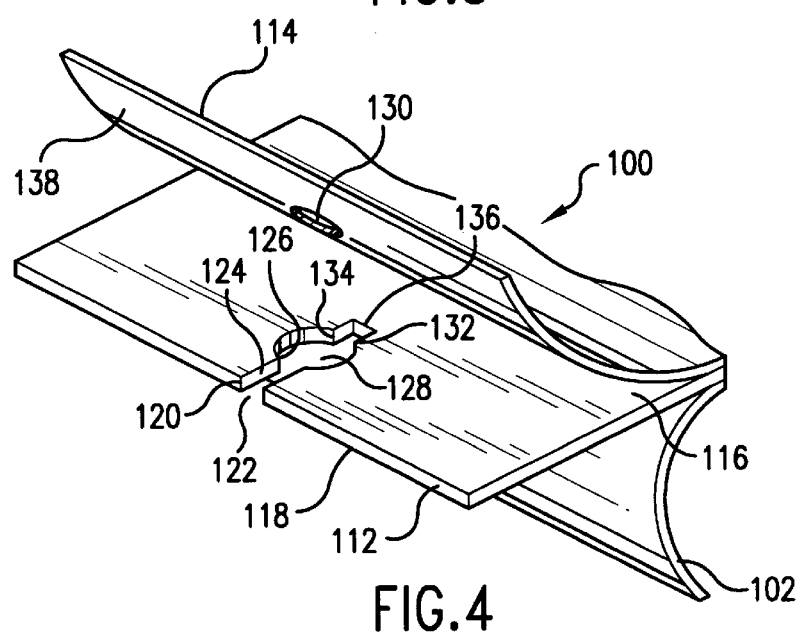
FIG. 4 is a partial perspective view of the embodiment shown in FIG. 3, with the layers shown peeled-apart. The view illustrates the functional portion of the article.
Figure 5:
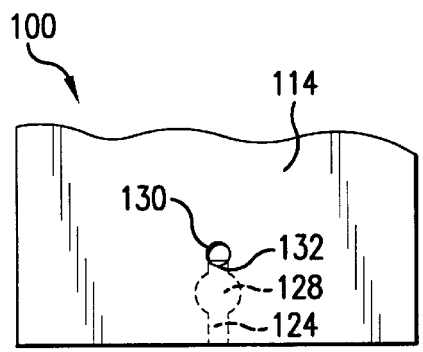
FIG. 5 is a partial top plan view of the article shown in FIGS. 3 and 4. The view illustrates the functional portion of the article.
Figure 6:
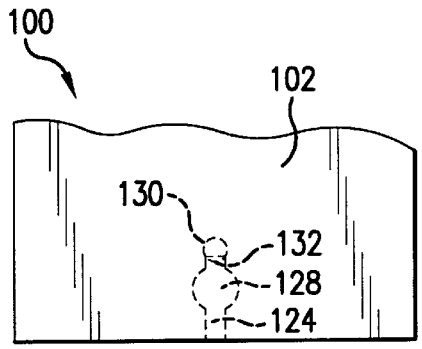
FIG. 6 is a partial bottom plan view of the article shown in FIGS. 3 and 4. The view illustrates the functional portion of the article. The view illustrates the functional portion of the article.
Figure 7:
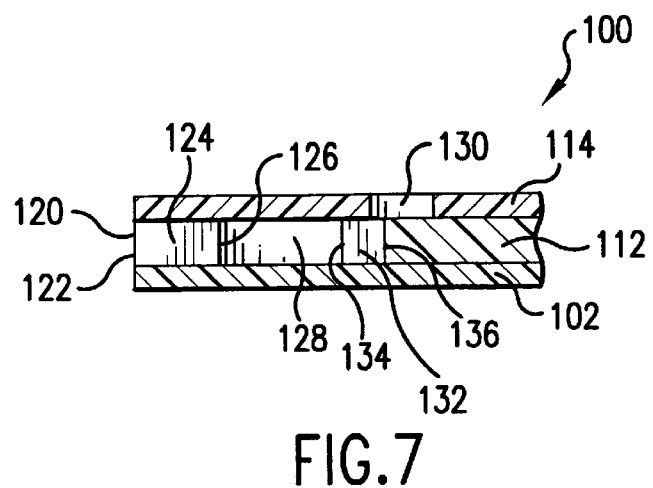
FIG. 7 is a partial cross-sectional view of the article shown in FIGS. 3 and 4. The view illustrates the functional portion of the article.

Referring now to FIGS. 1 and 2, the article 10 comprises a base layer 12, overlying the base layer 12 a core layer 14, and overlying the core layer 14 a cover layer 16. The core layer 14 has a first major surface 17 and a second major surface 18. The core layer 14 comprises an application site 20 communicating with a first end 22 of a flow channel 24. The flow channel 24 has a second end 26, which communicates with an optical reading chamber 28. The cover layer 16 has an opening 30, which serves as a vent. This embodiment requires a base layer 12 below the core layer 14, because the optical reading chamber 28 extends all the way through the core layer 14. A first major surface 38 of the cover layer 16 is in face-to-face contact with major surface 17 of the core layer 14. A first major surface 40 of the base layer 12 is in face-to-face contact with major surface 18 of the core layer 14.

Referring now to FIGS. 3, 4, 5, 6, and 7, the article 100 comprises a base layer 102, overlying the base layer 102 a core layer 112, and overlying the core layer 112 a cover layer 114. The core layer 112 has a first major surface 116 and a second major surface 118. The core layer 112 comprises an application site 120 communicating with a first end 122 of a flow channel 124. The flow channel 124 has a second end 126, which communicates with an optical reading chamber 128. The cover layer 114 has an opening 130, which serves as a vent. A vent channel 132 having a first end 134 that communicates with the optical reading chamber 128 and a second end 136 that communicates with the opening 130 is provided in the core layer 112. This embodiment requires a base layer 102 below the core layer 112, because the optical reading chamber 128 extends all the way through the core layer 112. A first major surface 138 of the cover layer 114 is in face-to-face contact with major surface 116 of the core layer 112. A first major surface 140 of the base layer 102 is in face-to-face contact with major surface 118 of the core layer 112.

Figure 8:
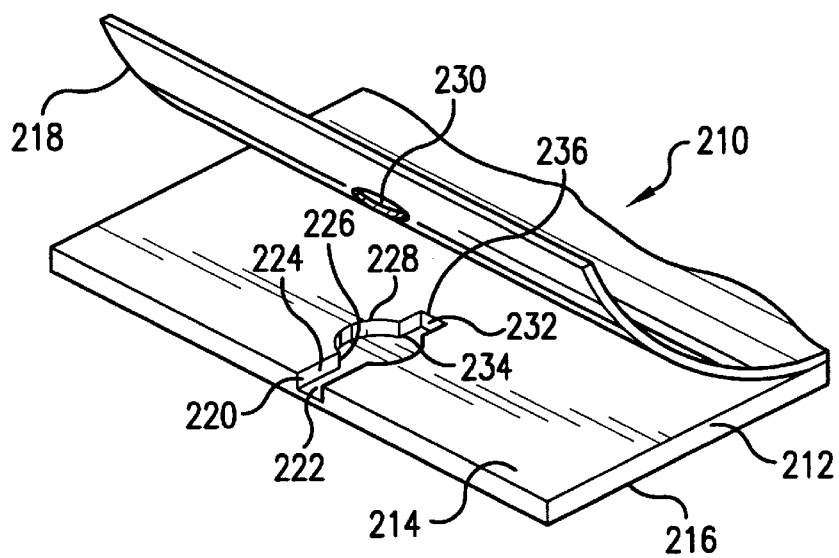
FIG. 8 is a partial perspective view of another embodiment of an article suitable for use in this invention, with the layers shown peeled apart. The view illustrates the functional portion of the article.
Figure 9:
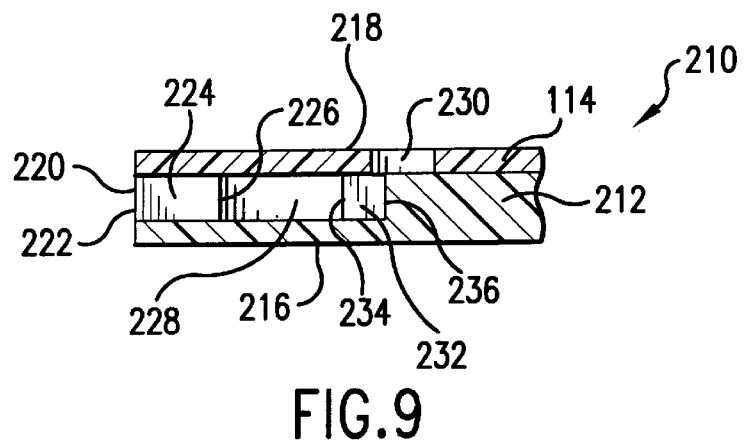
FIG. 9 is a partial cross-sectional view of the article shown in FIG. 8. The view illustrates the functional portion of the article.

Referring now to FIGS. 8 and 9, the article 210 comprises a base layer 212 having a first major surface 214 and a second major surface 216. Overlying the base layer 212 and in face-to-face contact with major surface 214 is a cover layer 218. The base layer 212 comprises an application site 220 communicating with a first end 222 of a flow channel 224. The flow channel 224 has a second end 226, which communicates with an optical reading chamber 228. The cover layer 218 has an opening 230, which serves as a vent. A vent channel 232 having a first end 234 that communicates with the optical reading chamber 228 and a second end 236 that communicates with the opening 230 is provided in the base layer 212. This embodiment does not require a third layer in face-to-face contact with major surface 216 of the base layer 212 because the application site 220, the flow channel 224, and the optical reading chamber 228 are elevated from major surface 16 of the base layer 212. The embodiment shown in FIGS. 3, 4, 5, 6, and 7 is preferred because it is easier to prepare in mass quantities.

Regardless of which embodiment is used, the surface dimensions of each layer are not critical, except to the extent that the dimensions must be selected so that the article will properly fit into an optical metering device. An example of surface dimensions suitable for an article of this invention having a rectangular surface are a length of 30 mm and a width of 20 mm. With respect to the preferred embodiment, an example of the thickness of the article is 0.3 mm. An example of the thickness of the base layer 102 is 0.1 mm. An example of the thickness of the cover layer 114 is 0.1 mm. An example of the thickness of the core layer 112 is 0.3 mm.

The portion of the cover layer and the portion of the base layer in register with the top and bottom of the optical reading chamber should be capable of transmitting light so that light transmitted through the article will not be obstructed from the reaction product. In the embodiment employing a core layer, the core layer need not be capable of transmitting light.

At least one of the base layer and cover layer must be hydrophilic. The core layer must not be capable of absorbing liquid. Materials that are suitable for preparing the core layer include glass and polymeric materials.

It should be noted that each of the named layers, i.e., the base layer, the core layer, and the cover layer, can comprise a single layer of material or, in the alternative, two or more layers of material joined together, as by adhesive, heat sealing, or some other means of lamination. However, it is preferred that each of the layers comprise a single layer of material on account of cost considerations, unless a composite layer would provide improved performance with respect to some parameter.

The optical reading chamber is capable of serving three functions: sample metering, reagent storing, and optical measurement. The volume of the optical reading chamber should be sufficiently large so that accurate optical measurement of concentration of analyte can be made. The volume of the optical reading chamber should be sufficiently small so that the volume of sample required for measurement can be extremely small. It is preferred that the volume of the optical reading chamber be less than about 1.0 $\mu$L, so that a small volume of sample will be sufficient. The shape of the optical reading chamber is not critical. However, it is preferred that the optical reading chamber be cylindrical in shape to bring about improved flow properties and reduction in the amount of sample required. Other shapes, e.g., rectangular, of the optical reading chamber can be used. It is preferred that the read area of the optical reading chamber be of a shape similar to the area of the light source. For example, if the light source is circular in shape, it is preferred that the optical reading chamber be cylindrical in shape. It is preferred that the depth of the optical reading chamber be selected so that the amount of sample required can be minimized.

The flow channel preferably has a rectangular cross-section, primarily because of ease of manufacture. The cross-section of the flow channel should be of a sufficient size so that a sufficient quantity of fluid can flow at a sufficient rate of flow even if random manufacturing defects are present in the flow channel. It is preferred that the dimensions of the cross-section of the flow channel be selected so that the depth of the flow channel is substantially equal to the depth of the optical reading chamber. If the depth of the flow channel is substantially greater than the depth of the optical reading chamber, a greater volume of sample may be required to carry out an assay. If the depth of the flow channel is substantially smaller than the depth of the optical reading chamber, manufacturing defects should significantly reduce the rate of flow of the sample. The width of the flow channel is selected so that the amount of sample required can be minimized. The length of the flow channel is selected so that the amount of sample required can be minimized. Other factors to be considered in selecting the dimensions of the flow channel include manufacturing problems and likelihood of evaporation of sample.

The vent channel preferably has a rectangular cross-section, primarily because of ease of manufacture. The vent channel should be of a sufficient length that evaporation of the sample in the vent channel does not adversely affect the optical reading chamber. An example of such an adverse effect is the presence of an air bubble in the optical reading chamber, which will result in erroneous absorbance readings. The volume of the vent channel is preferably made as small as possible in order to reduce the volume of the sample. The volume of the vent channel should be sufficiently great that air bubbles will not be formed in the optical reading chamber. The depth of the vent channel and the width of the vent channel are selected so that air bubbles will not be formed in the optical reading chamber.

Representative examples of dimensions of other features of the article of the preferred embodiment (FIGS. 3, 4, 5, 6, and 7) are as follows:

| Feature | Dimensions |
|---|---|
| Optical reading chamber | 1.5 mm diameter × 0.1 mm depth |
| Flow channel | 0.5 mm length × 0.5 mm width × 0.1 mm depth |
| Vent channel | 0.5 mm length × 0.5 mm width × 0.1 mm depth |
| Vent opening | 0.05 mm diameter |

Detection of analyte is carried out by measuring the change in an optical property of the material in the optical reading chamber resulting from one or more reactions involving the analyte with one or more reagents, whereby changes in absorbance can be observed by an optical instrument. In the case of determination of glucose, the reagents typically include at least one enzyme and at least one dye.

In one assay system for determining concentration of glucose, glucose in the sample is oxidized by glucose oxidase to form gluconic acid and $H_2O_2$. The amount of $H_2O_2$ produced is then measured quantitatively by Reaction (1) or Reaction (2).

Reaction (1)

Dye (colorless) + $H_2O_2$ $\xrightarrow{\text{Peroxidase}}$

Oxidized dye (colored) + $H_2O$

Reaction (2)

$H_2O_2 + Fe^{2+} \rightarrow Fe^{3+} + H_2O$ $Fe^{3+} + dye \rightarrow Fe^{3+}dye$ complex In Reaction (1), the enzyme peroxidase (e.g., horse radish peroxidase, microperoxidase) catalyzes the oxidation of the dye or converts $H_2O_2$ to $H_2O$. The color intensity is directly proportional to the concentration of glucose in the sample. Representative examples of dyes that have been used include o-dianisidine, 4-aminoantipyrine, and 3,5-dichloro-2-hydroxybenzenesulfonate.

In Reaction (2), $H_2O_2$ oxidizes the $Fe^{2+}$ to $Fe^{3+}$. $Fe^{3+}$ then chelates with dye to produce a specific absorption peak. Representative examples of ferrous salt include ferrous sulfate and potassium ferrocyanide. Representative examples of the dye include xylenol orange. The amount of $Fe^{3+}$ dye complex that forms is proportional to the amount of glucose in the sample.

In another assay system for determining concentration of glucose, which is preferred for this invention, glucose dehydrogenase enzyme reacts specifically with glucose in the sample in the presence of co-enzyme β-nicotinamide adenine dinucleotide (β-NAD) to form NADH, the reduced form of +β-NAD. The NADH reacts with an electron accepting dye, e.g., 3-[4,5-dimethylthiazol-2-yl]-2,5-diphenyltetrazolium bromide (MTT), catalyzed by the diaphorase enzyme to form a dark purple-reddish color. The color intensity measured at 640 nm is directly proportional to the concentration of glucose in the sample.

Glucose + β-NAD $\xrightarrow{\text{Glucose dehydrogenase}}$ Gluconic acid + NADH NADH + MTT (yellow) $\xrightarrow{\text{Diaphorase}}$ MTT (purple-reddish) + β-NAD In both systems, detection is carried out by means of optical measurement. The measurement can be of absorbance, reflectance, or transmittance. It is preferred that absorbance be employed. The specimens suitable for the method include, but are not limited to, blood, plasma, serum, interstitial fluid, urine.

Operation

Samples of interstitial fluid can be obtained from a patient by any of a variety of methods, which are well-known to one of ordinary skill in the art. Such methods include, but are not limited to, those described in U.S. Pat. Nos. 4,775,361; 5,423,803; WO 94/09713; and WO 97/07734, all of which are incorporated herein by reference.

The multiple-layer element preferably contains a dried reagent in the optical reading chamber 128. The sample obtained from the patient is introduced to the multiple-layer element at the application site 120. After introduction to the element, the liquid sample flows through the flow channel 124 into the optical reading chamber 128 and from the optical reading chamber 128 to the end of the vent channel 132. The fluid ceases flowing when it reaches the opening 130. The liquid sample rehydrates the dried reagent in the optical reading chamber, which then reacts with the analyte of interest. The reaction occurs in the optical reading chamber. The flow through flow channel 124 can be characterized as capillary flow, i.e., flow that is driven by capillary attraction, which can be defined as the force that results from greater adhesion of a liquid to a solid surface than internal cohesion of the liquid itself. Alternatively, if the multiple-layer element does not contain a dried reagent in the optical reading chamber, the sample obtained from the patient can be mixed with the reagent, and the resulting mixture introduced to the multiple-layer element at the application site 120. After introduction to the element, the reaction mixture flows through the flow channel 124, by means of capillary flow into the optical reading chamber 128 and from the optical reading chamber 128 to the end of the vent channel 132. The reaction mixture ceases flowing when it reaches the opening 130. The reaction occurs prior to the entrance of the reaction mixture to the optical reading chamber.

Figure 16:
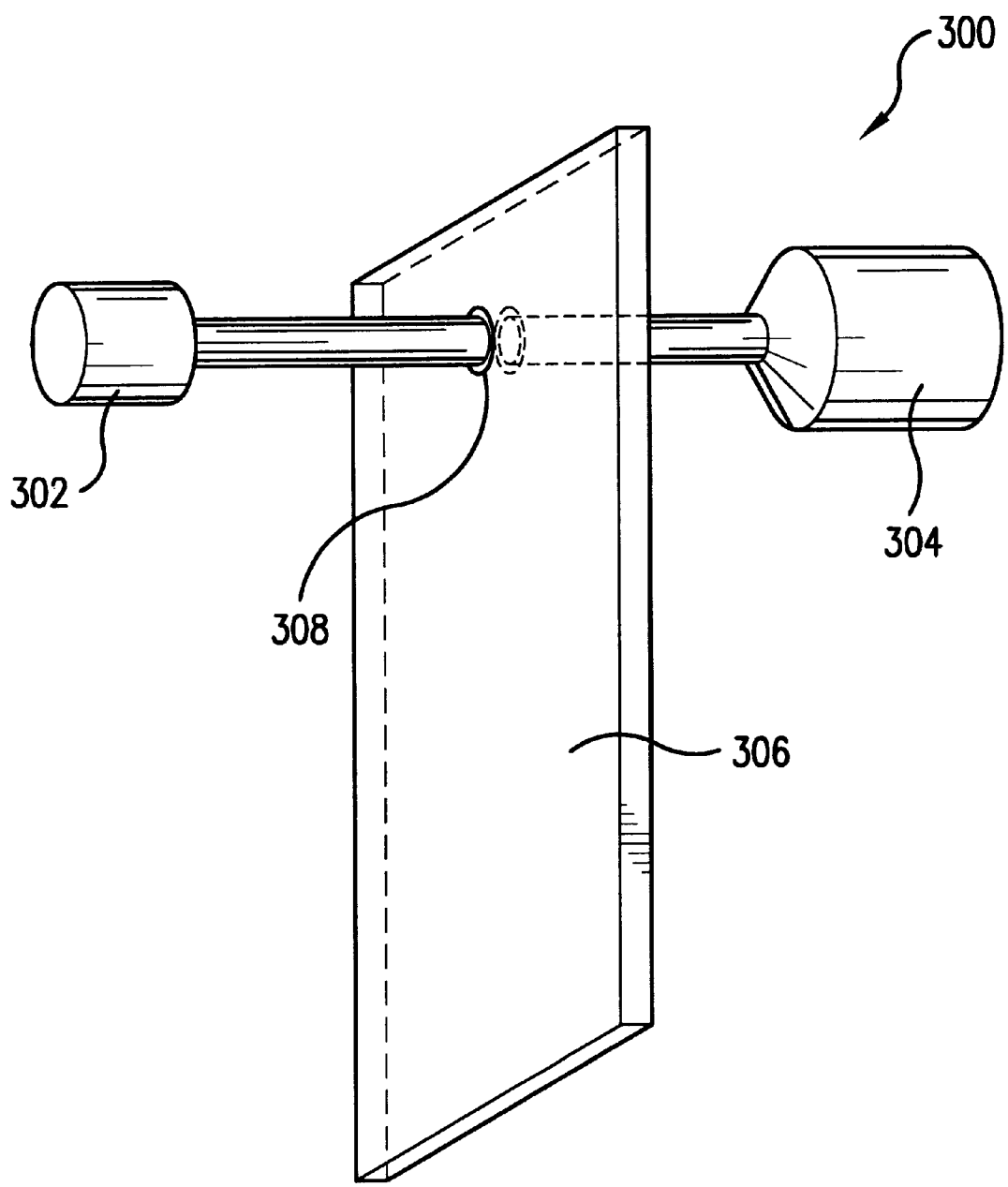
FIG. 16 is a schematic diagram of an instrument suitable for reading optical properties of the article of this invention.

Regardless of how the sample and the reagents are introduced into the article, the optical readings are taken when the reaction product, i.e., the product of reaction between the reagent and the analyte, is finally located in the optical reading chamber. The optical reading is typically an absorbance reading. FIG. 16 shows an apparatus suitable for measuring absorbance. The apparatus 300 comprises a source of light 302 and a detector 304. The multiple-layer element 306 is disposed between the source of light 302 and the detector 304. The optical reading chamber 308 in the multiple-layer element 304 is aligned with the light from the source of light 302 and the detector 304 so that the light from the source of light 302 is transmitted through the optical reading chamber 308 and detected by the detector 304. The source of light 302 preferably has a wavelength of from about 500 nm to about 700 nm. A preferred source of light is a light emitting diode. The detector 304 is preferably a photodetector, and the readings are usually reported in volts.

The element of the present invention provides several significant advantages. First, only a very low volume of sample is required for carrying out the assay. Second, the fluid transfer does not require precision pipetting. In addition, the results of the assay can be read optically. Optical reading can provide more accurate results than can results read electronically. Furthermore, the article can be constructed so that evaporation of the sample can be minimized. The particular reagents that are used in the article and method of this invention are capable of reacting under low oxygen conditions, with the result that the results are accurate, sensitive, and reproducible.

The utilization of capillary flow for filling the optical reading chamber allows the elimination of the need for external force to fill the optical reading chamber, thereby eliminating the need for pumps, motors, tubing, and the like.

The article and method of this invention can be adapted for measuring the concentration of analytes other than glucose. Such analytes include, for example, cholesterol, uric acid, BUN (blood urea nitrogen), and creatinine.

The following non-limiting examples are intended to further illustrate the invention.

EXAMPLES

Example 1

This example demonstrates the feasibility of a glucose assay wherein the sample size was less than 25 µL.

The following materials were purchased from Sigma Chemical Company:
  Glucose oxidase
  Horseradish peroxidase
  4-Aminoantipyrine
  3, 5-Dichloro-2-hydroxy-benzenesulfonic acid
  Sodium phosphate
Glucose was purchased from EM Sciences.

The absorbance of the reaction product was read at 515 nm in a Hewlett Packard Diode Array Spectrophotometer (model 8452A). The multiple-layer elements 400 used in this example were of the type depicted in FIGS. 1 and 2. The element shown in FIGS. 1 and 2 is substantially similar to that shown in FIGS. 3, 4, 5, 6, and 7 with the exceptions that the optical reading chamber has a different size and a different geometric shape. The core layer 14 of the multiple-layer element 10 was 0.33 mm thick. The cover layer 16 and the base layer 12 of the multiple-layer element 400 were 0.11 mm thick. The cover layer 16 and the base layer 12 were adhered to opposite major surfaces of the core layer 14 by means of adhesive. The cover layer 16 and the base layer 12 of the multiple-layer element 10 were made of polycarbonate. The core layer 14 of the multiple-layer element 10 was made of polyester. The dimensions of the surface of the element were 10 mm wide by 30 mm long. The dimensions of the optical reading chamber 28 were 7.7 mm×9.6 mm×0.33 mm. The volume of the optical reading chamber 28 was about 24.4 µL.

The reagents used in the assay were prepared as follows:

| | |
|---|---|
| Buffer: | 50 mM phosphate, pH 7.0 |
| Enzyme solution: | horseradish peroxidase (2 units/µL) and glucose oxidase (2 units/µL) were dissolved in 50 mM phosphate, pH 7.0 (stock solution) |
| Dye solution: | a mixture of 0.5M of 4-aminoantipyrine and 0.5M 3, 5-dichloro-2-hydroxy-benzenesulfonate in 50 mM phosphate buffer, pH 7.0 (stock solution) |
| Glucose solution: | glucose solutions contained 0, 31.1, 62.2, 125, 250 mg/dL prepared in 50 mM phosphate buffer, pH 7.0 |

To glucose solution (1.0 mL) was added enzyme solution (20 µL) and dye solution (50 µL). The reaction was carried out at room temperature for two minutes. The reaction mixture was then drawn into the optical reading chamber by capillary attraction and the absorbance of the reaction mixture read at 515 nm. The following table shows the absorbance of the reaction mixture at various concentrations of glucose.

TABLE 1

| Concentration of glucose (mg/dL) | Absorbance |
|---|---|
| 0 | 0.09 |
| 31.1 | 0.34 |
| 62.2 | 0.71 |
| 125.0 | 1.38 |
| 250.0 | 2.39 |

Figure 10:
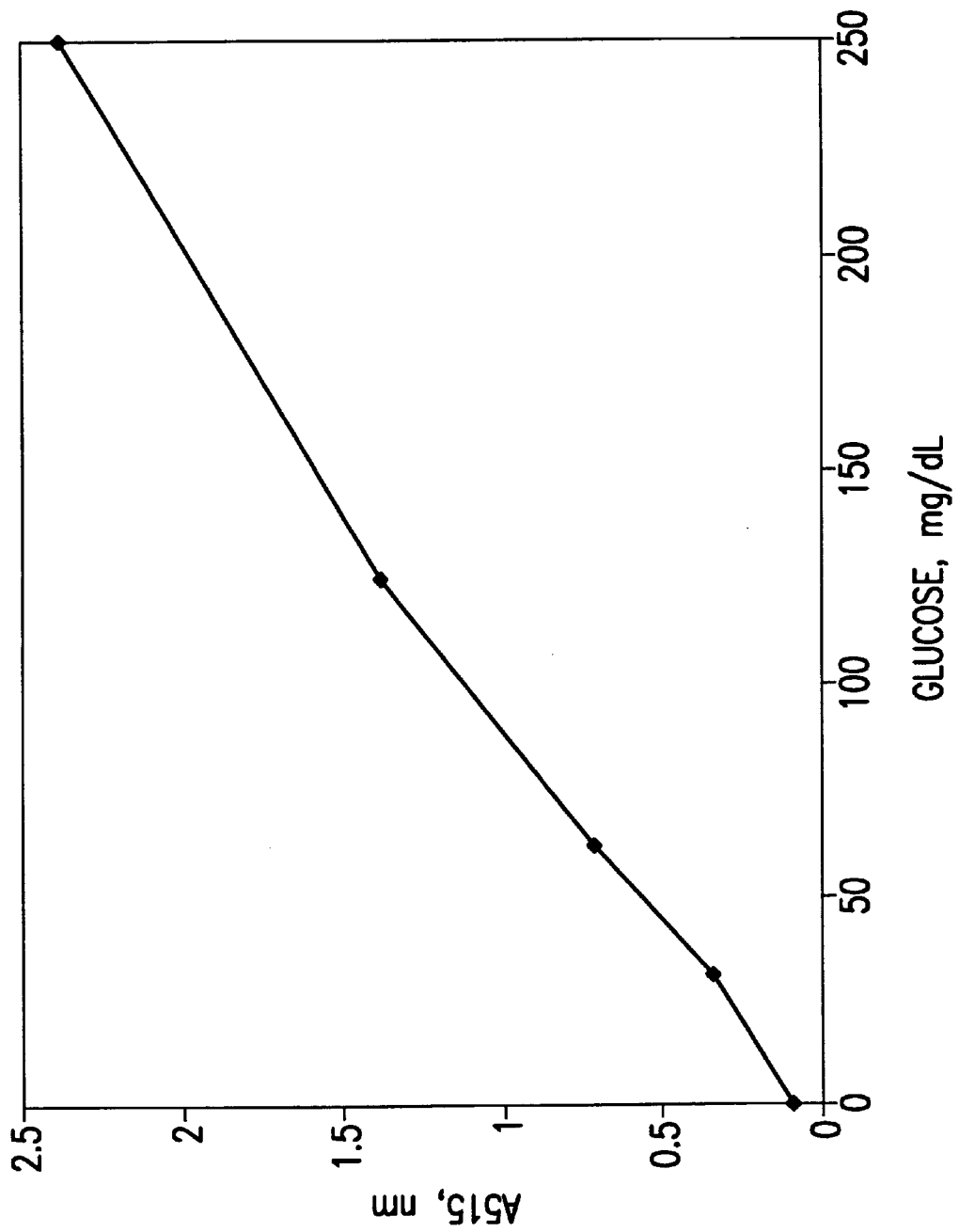
FIG. 10 is a graph illustrating absorbance at 515 nm of a glucose solution as a function of glucose concentration.

FIG. 10 illustrates the dose response curve for this example. From the data in TABLE 1 and the dose response curve, it can be seen that the article and method of this example provide a linear response. A linear dose response is preferred because such a response simplifies calculation of concentration of analyte.

Example 2

This example demonstrates the feasibility of a glucose assay utilizing a small volume of sample.

The following materials were purchased from Sigma Chemical Company.

Tris (hydroxymethyl) aminomethane buffer (hereinafter "Tris buffer")

$MgCl_2 \cdot 6H_2O$

Adenosine 5'-triphosphate (ATP)

β-Nicotinamide adenine dinucleotide (β-NAD)

3-[4,5-dimethylthiazol-2-yl]-2,5-diphenyltetrazolium bromide (MTT)

Hexokinase

Glucose 6-phosphate dehydrogenase (G-6-PDH)

Diaphorase

Glucose was purchased from EM Sciences.

The following compounds were weighed and dissolved in 1.3 mL of 0.2 M Tris buffer, pH 7.0:

| | |
|---|---|
| $MgCl_2 \cdot 6H_2O$ | 0.0276 g |
| ATP | 0.0165 g |
| β-NAD | 0.0189 g |
| MTT | 0.030 g |
| Hexokinase | 75 units |
| G-6-PDH | 75 units |
| Diaphorase | 75 units |

The reagent was prepared in the following manner. The MTT was first dissolved in the Tris buffer. β-NAD and ATP were then added to the solution and dissolved. The pH of the resulting solution was then readjusted to 7.0 by means of a 1.0 M Tris solution. The remaining components were then added and the resulting mixture was mixed.

The multiple-layer element used in this example was of the type shown in FIGS. 3, 4, 5, 6, and 7. The features of the multiple-layer element had the following dimensions:

TABLE 2

| Feature | Dimensions |
|---|---|
| Optical reading chamber | 1.5 mm diameter × 0.3 mm depth |
| Flow channel | 0.5 mm × 1.0 mm × 0.3 mm depth |
| Vent channel | 0.5 mm × 0.5 mm × 0.3 mm depth |
| Vent opening | 0.05 mm diameter |
| Cover layer | 12 mm × 30 mm × 0.1 mm |
| Base layer | 12 mm × 30 mm × 0.1 mm |
| Core layer | 12 mm × 30 mm × 0.3 mm |

Figure 11:
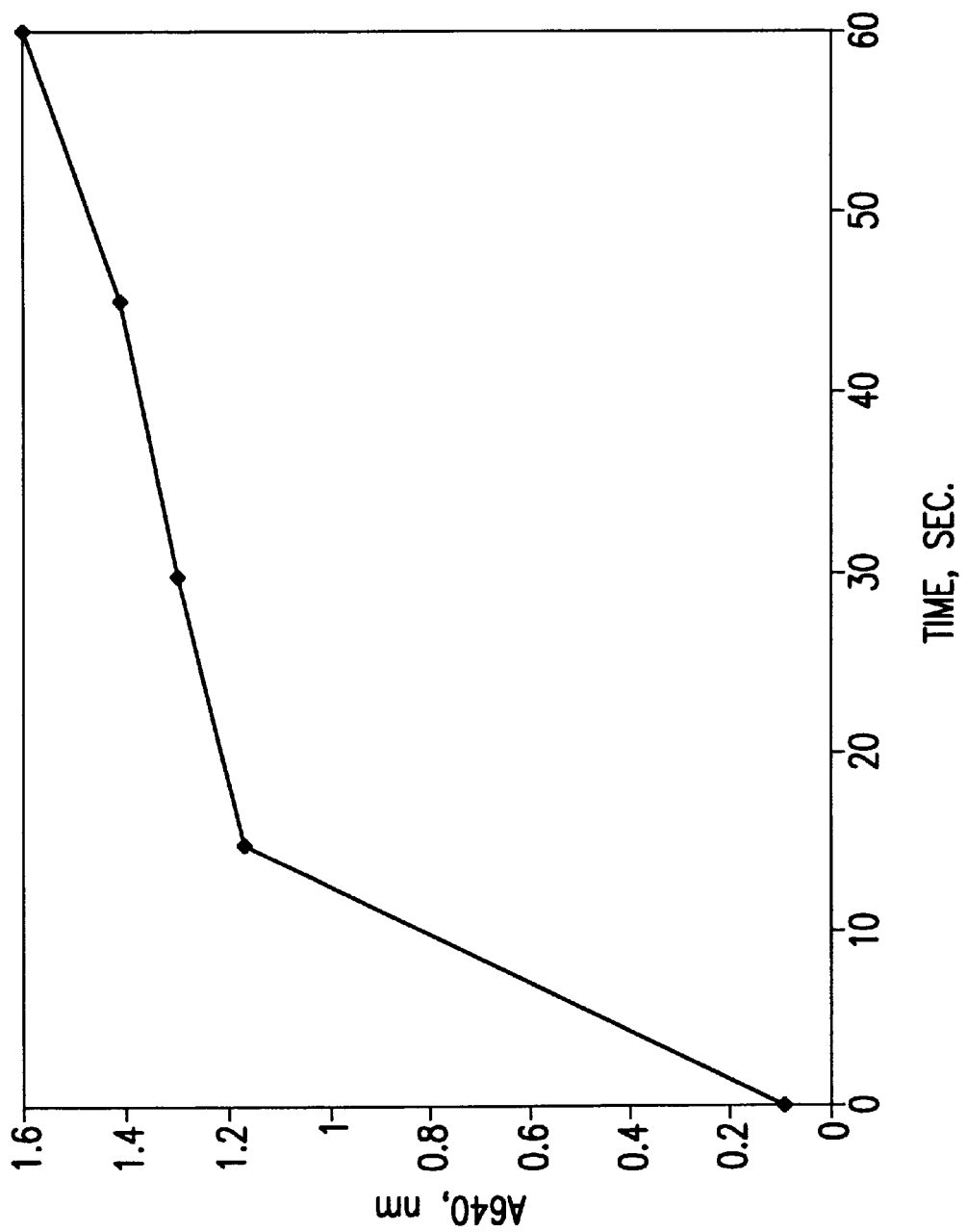
FIG. 11 is a graph illustrating absorbance at 640 nm of a glucose solution as a function of glucose concentration.

Reagent (0.3 μL) was introduced into the multiple-layer element at the application site by means of capillary attraction. Glucose solution (0.3 μL, 250 mg/dL) was then introduced into the multiple-layer element at the application site by means of capillary attraction. The final reaction volume was 0.582 μL. The rate of reaction was monitored in a Hewlett Packard Diode Array Spectrophotometer (model 8452A) at 640 nm. The reaction was complete in about two minutes at room temperature. FIG. 11 illustrates absorbance as a function of time. It can be seen that the rate of change in absorbance as a function of time decreases after about 15 seconds.

Example 3

This example demonstrates the nature of dose response of a glucose assay utilizing a multiple-layer element having the same dimensions as the element described in Example 2. The reagent employed was the same as that described in Example 2.

The result of each reaction was read after two minutes. Standard glucose solutions were used. A linear glucose response curve was obtained.

Figure 12:
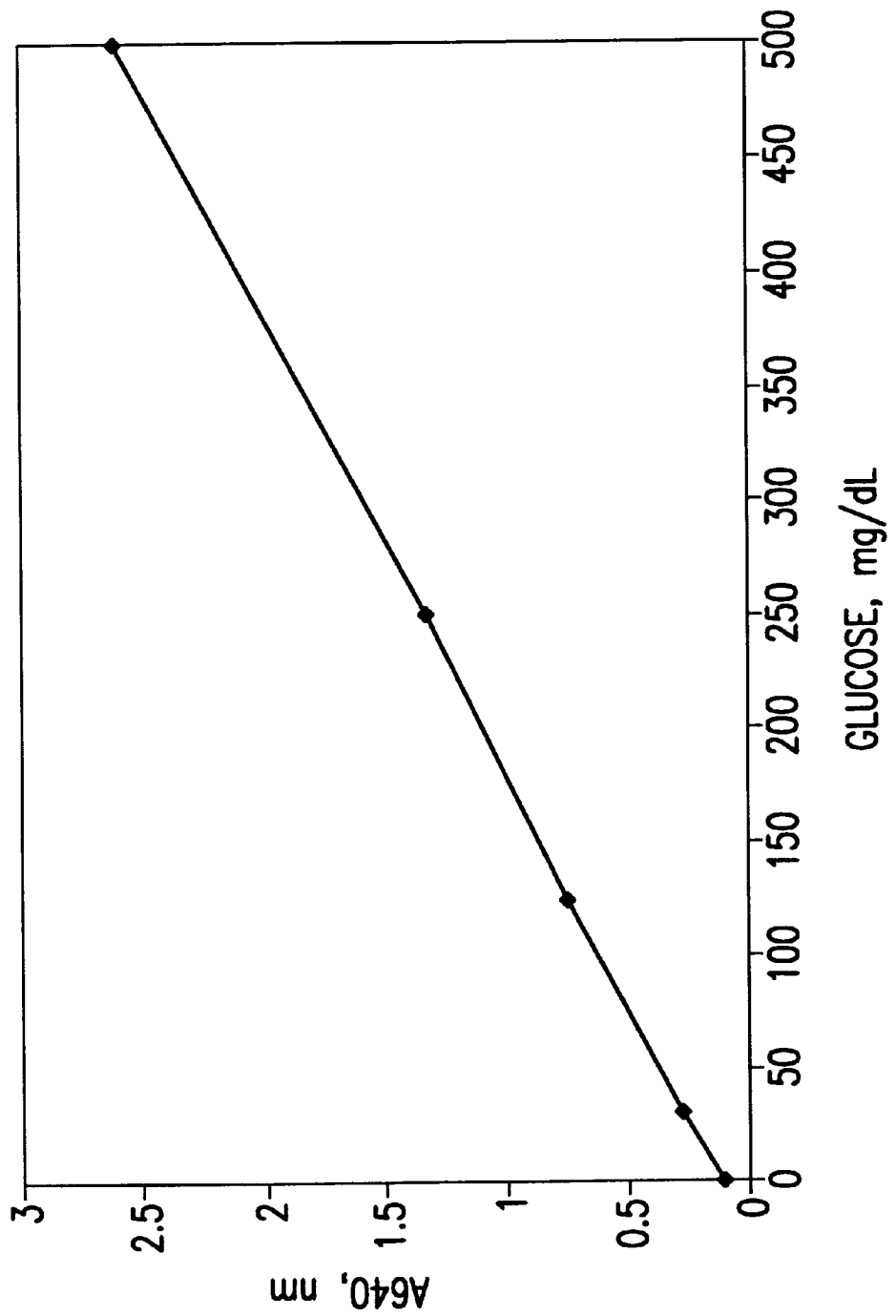
FIG. 12 is a graph illustrating absorbance at 640 nm of a glucose solution as a function of glucose concentration.

FIG. 12 illustrates absorbance at 640 nm as a function of glucose concentration. From FIG. 12, it can be seen that the article and method of this example provide a linear dose response.

Example 4

This example demonstrates a glucose assay utilizing a small volume of sample and a volume of optical reading chamber of 0.251 μL.

The materials and multiple-layer element of the type described in Example 2 were employed. The dimensions of the optical reading chamber were 1.5 mm diameter, 0.10 mm depth. The flow channel and the vent channel were 0.5 mm in width, 0.5 mm in length, and 0.1 mm in depth.

Reagent (10 μL) (from Example 2) was mixed with glucose solution (10 μL). The resulting mixture was introduced into the element at the sample application site by means of capillary attraction. Absorbance readings at 640 nm were taken after two minutes. Sufficient runs were carried out to prepare a dose response curve.

A linear glucose dose response curve was obtained. The curve is described by the formula $y=3.003x+179.24$; $r^2=0.9887$. The hexokinase/G-6-PDH/Diaphorase/MTT system gave a detection sensitivity of about 3 mA/mg/dL of glucose. The reproducibility of the multiple-layer element was tested by reading the absorbance of the reaction mixture of the same glucose solution in six different elements. As can be seen from TABLE 3, CV of 7.02 was obtained at about 173 mg/dL of glucose.

TABLE 3

| Run no. | Concentration of glucose (mg/dL) |
|---|---|
| 1 | 187 |
| 2 | 170 |
| 3 | 164 |
| 4 | 164 |
| 5 | 164 |
| 6 | 190 |

Mean=173

S. D.=12.14

CV%=7.02

Figure 13:
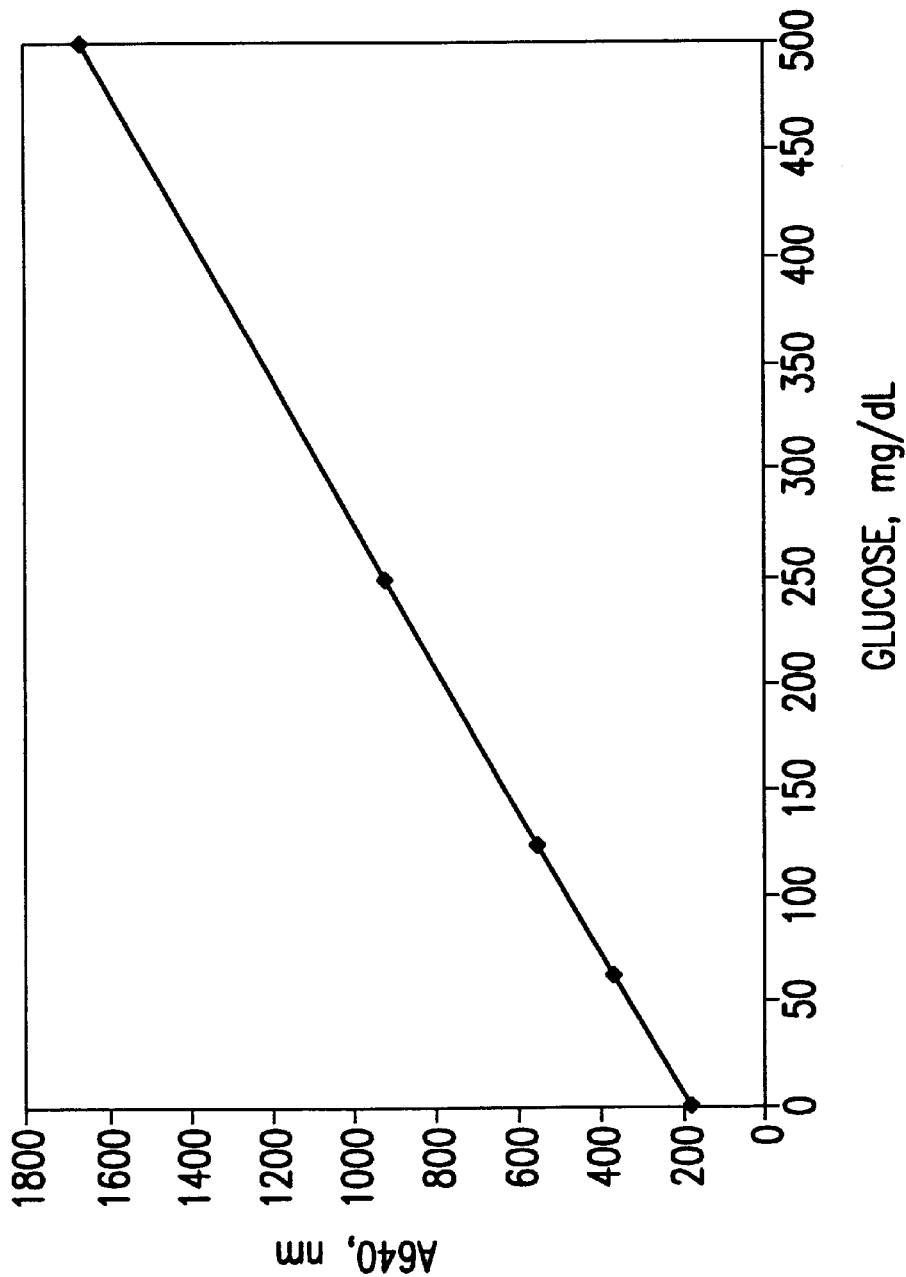
FIG. 13 is a graph illustrating absorbance at 640 nm of a glucose solution as a function of glucose concentration.

FIG. 13 illustrates that a linear dose response was obtained. From the data of this example, it can be seen that there was low variation from sample to sample.

Example 5

This example demonstrates a glucose assay utilizing a small volume of sample and multiple-layer elements containing reagent in a dried state. Elements of the type described in Example 2 were used. However, in each element, only the base layer had been laminated to one major surface of the core layer. The other major surface of the core layer had been left uncovered so that reagent could be deposited into the optical reading chamber.

The reagent was prepared as described in Example 2. Reagent (0.5 μL) was transferred by pipette into the optical reading chamber of each multiple-layer element. The reagent was allowed to dry at room temperature. The remaining major surface of the core layer was then laminated to one major surface of the cover layer. The cover layer contained a small opening for vent. The thus-formed multiple-layer elements were then stored in a container containing silica.

In order to conduct the assay, the glucose solution was introduced into the multiple-layer element at the application site by means of capillary attraction. The volume of each sample was 0.25 µL. When the fluid reached the vent opening, the flow of fluid ceased. The results of the reaction were read at 640 nm at room temperature after one minute. Sufficient runs were carried out to prepare a dose response curve.

Figure 14:
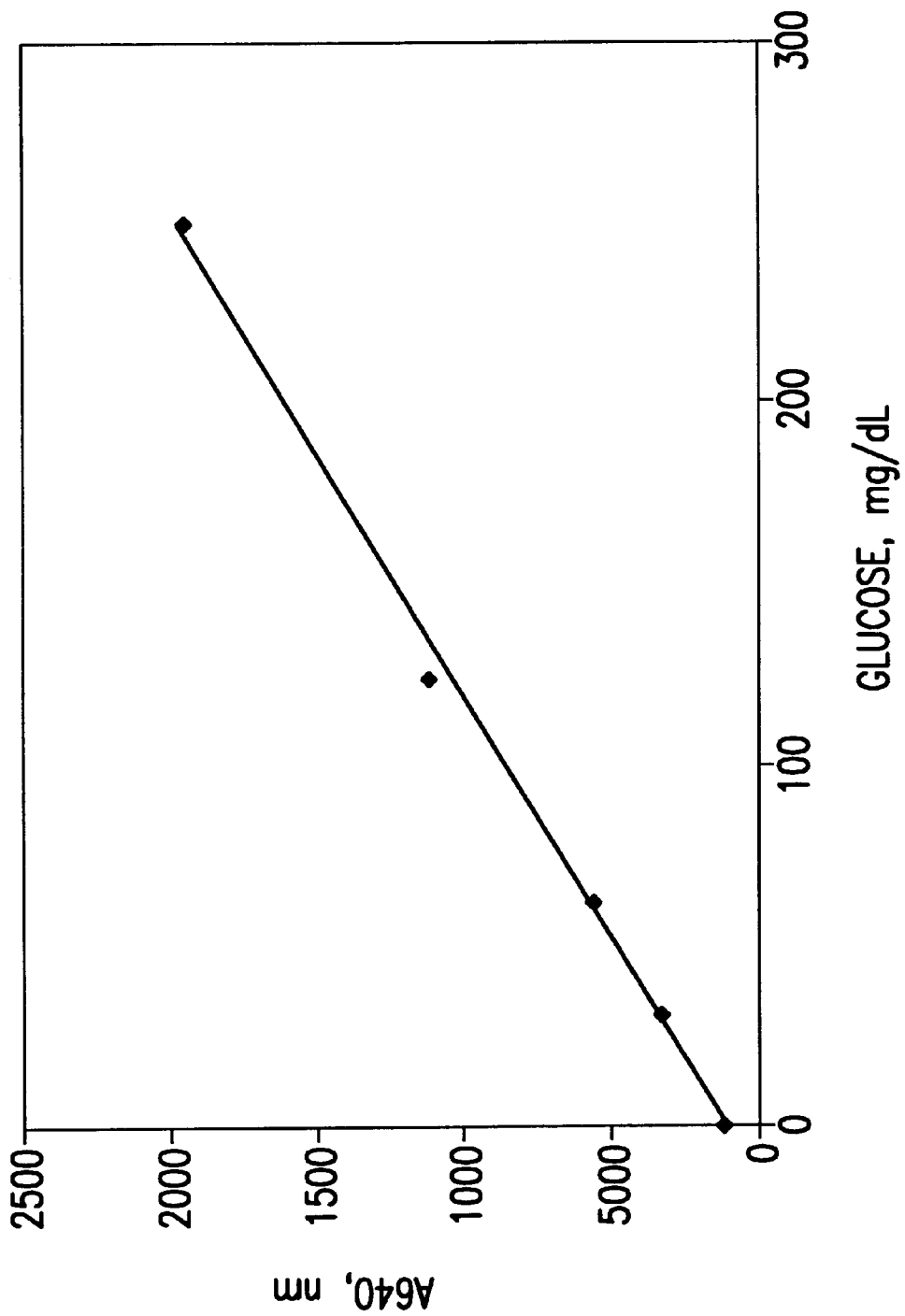
FIG. 14 is a graph illustrating absorbance at 640 nm of a glucose solution as a function of glucose concentration.

FIG. 14 illustrates current (the absorbance signal) as a function of glucose concentration. The data in FIG. 14 shows that the article and method of this example provide a linear dose response.

Example 6

This example demonstrates the feasibility of a glucose assay utilizing a small volume of sample with an enzyme system comprising glucose dehydrogenase and diaphorase.

The following materials were purchased from Sigma Chemical Company:
Tris buffer
$MgCl_2.6H_2O$
β-Nicotinamide adenine dinucleotide (β-NAD)
3-[4,5-dimethylthiazol-2-yl]-2,5-diphenyltetrazolium bromide (MTT)
Glucose dehydrogenase
Diaphorase
Glucose was obtained from EM Sciences.

The enzyme system was prepared in the following manner. MTT (3 mg) was dissolved in 100 mM Tris buffer (200 µL), pH 7.0. β-NAD (12 mg) was then added to the solution and allowed to dissolve. To this mixture was added 1.0 M $MgCl_2.6H_2O$ (2 µL). The pH of the solution was adjusted to 7.0 by means of 1.0 M Tris buffer. To this mixture was then added glucose dehydrogenase (5 mg, 75 units/mg) and 15 units of diaphorase.

Figure 15:
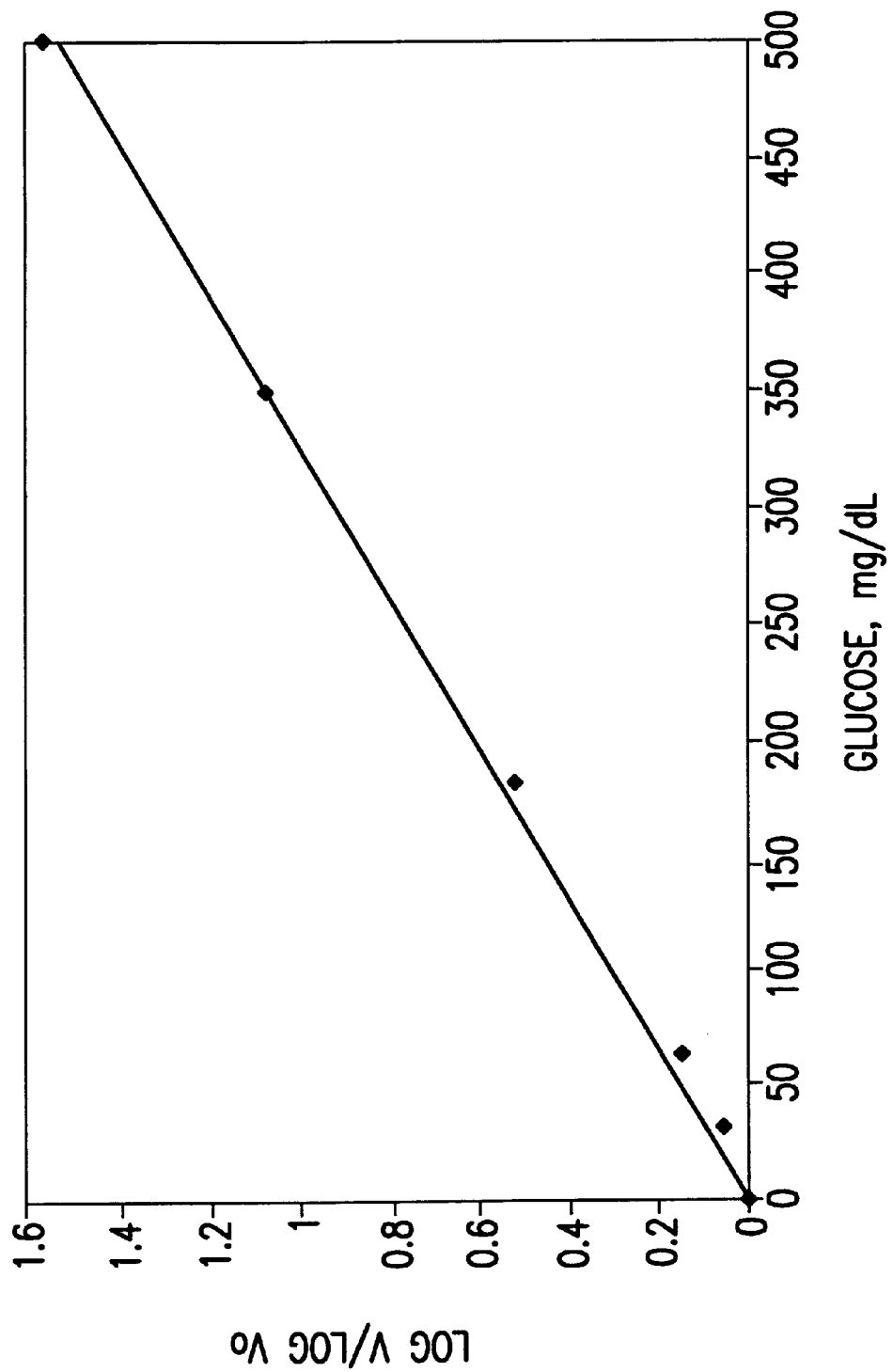
FIG. 15 is a graph illustrating absorbance at 640 nm of a glucose solution as a function of glucose concentration.

The reagent (3 µL) mixed with glucose solution (3 µL) was introduced by means of capillary attraction into an element of the type described in Example 2. The absorbance of the reaction product was measured at 650 nm using the instrument shown in FIG. 16. Sufficient runs were carried out to prepare a dose response curve. FIG. 15 shows a linear glucose dose response up to 500 mg/dl with a detection sensitivity of 35 mg/dL.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An article for determining the presence or amount of analyte in a biological sample, said article comprising a multiple-layer element comprising:
   (a) a base layer having two major surfaces, said base layer further having an opening, a flow channel, and an optical reading chamber, one end of which flow channel communicates with said opening in said base layer and the other end of which flow channel communicates with said optical reading chamber; and
   (b) a cover layer in face-to-face contact with the major surface of said base layer containing said opening, said cover layer having an opening therein to vent said element.

2. The article of claim 1, wherein said optical reading chamber does not extend completely through said base layer.

3. The article of claim 1, wherein said optical reading chamber contains at least one reagent with which the analyte in the sample reacts to form an optically detectable reaction product.

4. The article of claim 3, wherein said at least one reagent comprises hexokinase.

5. The article of claim 3, wherein said at least one reagent comprises glucose dehydrogenase.

6. The article of claim 3, wherein said at least one reagent comprises diaphorase.

7. The article of claim 1, wherein said second opening communicates with a vent channel.

8. The article of claim 1, wherein said optical reading chamber is cylindrical in shape.

9. The article of claim 1, wherein said optical reading chamber has a volume no greater than about 1 µL.

10. The article of claim 1, wherein said cover layer has a portion capable of transmitting light in register with said optical reading chamber.

11. The article of claim 1, wherein said base layer has a portion capable of transmitting light in register with said optical reading chamber.

12. The article of claim 1, wherein said second opening is not directly over said optical reading chamber.

13. An article for determining the presence or amount of analyte in a biological sample, said article comprising a multiple-layer element comprising;
   (a) a core layer having two major surfaces, said core layer further having an opening, a flow channel, and an optical reading chamber, one end of which flow channel communicates with said opening in said core layer and the other end of which flow channel communicates with said optical reading chamber; and
   (b) a base layer in face-to-face contact with one major surface of said core layer; and
   (c) a cover layer in face-to-face contact with the other major surface of said core layer, said cover layer having an opening therein to vent said element.

14. The article of claim 13, wherein said optical reading chamber extends completely through said core layer.

15. The article of claim 13, wherein said optical reading chamber contains at least one reagent with which the analyte in the sample reacts to form an optically detectable reaction product.

16. The article of claim 15, wherein said at least one reagent comprises hexokinase.

17. The article of claim 15, wherein said at least one reagent comprises glucose dehydrogenase.

18. The article of claim 15, wherein said at least one reagent comprises diaphorase.

19. The article of claim 13, wherein said second opening communicates with a vent channel.

20. The article of claim 13, wherein said optical reading chamber is cylindrical in shape.

21. The article of claim 13, wherein said optical reading chamber has a volume no greater than about 1 µL.

22. The article of claim 13, wherein said cover layer has a portion capable of transmitting light in register with said optical reading chamber is transparent.

23. The article of claim 13, wherein said base layer has a portion capable of transmitting light in register with said optical reading chamber.

24. The article of claim 13, wherein said second opening is not directly over said optical reading chamber.

25. A method for measuring the concentration of analyte in a sample comprising the steps of:
   (a) obtaining a sample of biological fluid from the body of a patient;
   (b) introducing the sample to the article of claim 1;
   (c) allowing at least one reagent in the article to react with the analyte of interest in the sample; and (d) measuring the concentration of analyte in the sample by optical instrument.

26. The method of claim 25, wherein the biological fluid is interstitial fluid.

27. The method claim 25, wherein said at least one reagent comprises hexokinase.

28. The method claim 25, wherein said at least one reagent comprises glucose dehydrogenase.

29. The method claim 25, wherein said at least one reagent comprises diaphorase.

30. A method for measuring the concentration of analyte in a sample comprising the steps of:
   (a) obtaining a sample of biological fluid from the body of a patient;
   (b) introducing the sample to the article of claim 13;
   (c) allowing at least one reagent in the article to react with the analyte of interest in the sample; and
   (d) measuring the concentration of analyte in the sample by optical instrument.

31. The method of claim 30, wherein the biological fluid is interstitial fluid.

32. The method claim 30, wherein said at least one reagent comprises hexokinase.

33. The method claim 30, wherein said at least one reagent comprises glucose dehydrogenase.

34. The method claim 30, wherein said at least one reagent comprises diaphorase.

* * * * *

(12) EX PARTE REEXAMINATION CERTIFICATE (6149th)
United States Patent
Wong et al.

(10) Number: US 6,077,660 C1
(45) Certificate Issued: *Mar. 11, 2008

(54) DIAGNOSTIC ASSAY REQUIRING A SMALL SAMPLE OF BIOLOGICAL FLUID

(75) Inventors: Sie Ting Wong, Mundelein, IL (US); Robert G. Hiltibran, Bristol, WI (US); Tung-Ming Huang, Buffalo Grove, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Reexamination Request:
No. 90/007,928, Feb. 13, 2006

Reexamination Certificate for:
Patent No.: 6,077,660
Issued: Jun. 20, 2000
Appl. No.: 09/095,683
Filed: Jun. 10, 1998

(51) Int. Cl.
*G01N 33/53* (2006.01)
*G01N 33/543* (2006.01)

(52) U.S. Cl. .............................. 435/4; 435/14; 435/26; 435/283.1; 435/289.1; 422/50; 422/55

(58) Field of Classification Search .................. None
See application file for complete search history.

(56) References Cited

U.S. PATENT DOCUMENTS 4,323,536 A  4/1982  Columbus (Continued)

FOREIGN PATENT DOCUMENTS

EP  0 138 152 B1  4/1985

(Continued)

OTHER PUBLICATIONS

CoaguChek® PT Test in Vitro Diagnosticum, Boehringer Mannheim, Jun. 30, 1996, Germany.

(Continued)

*Primary Examiner*—Sharon L. Turner

(57) ABSTRACT

An article and a method for monitoring the concentration of glucose in blood. In one aspect, the invention involves an article comprising a multiple-layer element utilizing reagents capable of reacting with an analyte of interest. In a preferred embodiment, the element comprises:

(a) a core layer having two major surfaces, an optical reading chamber extending from a first opening in one of the two major surfaces to a second opening in the other of the two major surfaces, the core layer further having a third opening therein and a flow channel, one end of which flow channel communicates with the third opening and the other end of which flow channel communicates with the optical reading chamber;

(b) a base layer in face-to-face contact with one major surface of the core layer; and (c) a cover layer in face-to-face contact with the other major surface of the core layer, the cover layer having an opening therein to vent the element.

In another aspect, the invention involves a method comprising the steps of:

(a) obtaining a sample of biological fluid, e.g., interstitial fluid, from the body of a patient;

(b) introducing the sample to an article comprising a multiple-layer element having an optical reading chamber;

(c) allowing reagents to react with an analyte of interest in the sample; and (d) measuring the concentration of analyte in the sample by means of an optical instrument.

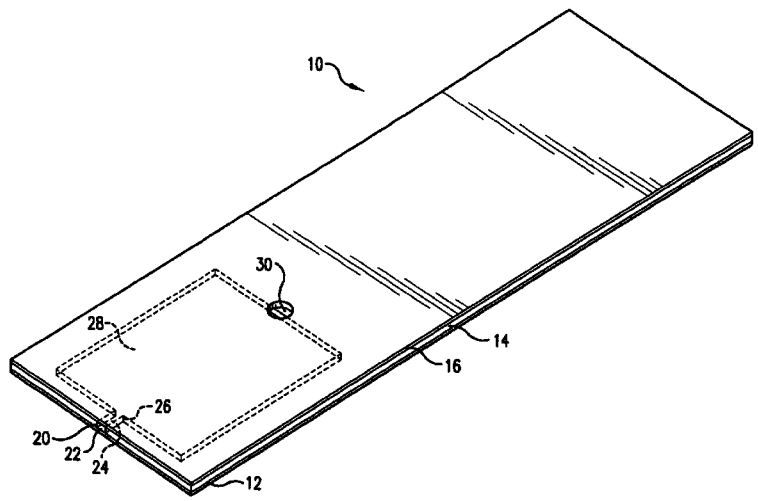

U.S. PATENT DOCUMENTS

| | | | |
|---|---|---|---|
| 4,849,340 A | | 7/1989 | Oberhardt |
| 5,000,922 A | * | 3/1991 | Turpen ........................ 422/101 |
| 5,161,532 A | * | 11/1992 | Joseph ........................ 600/345 |
| 5,437,999 A | | 8/1995 | Diebold et al. |
| 6,180,062 B1 | * | 1/2001 | Naka et al. .................... 422/81 |

FOREIGN PATENT DOCUMENTS

| | | |
|---|---|---|
| EP | 0 287 883 A1 | 10/1988 |
| EP | 0 502 504 B1 | 9/1992 |
| EP | 0 878 708 B1 | 11/1998 |
| GB | 2 090 659 A | 7/1982 |
| WO | 96/03318 | 2/1996 |
| WO | 99/30152 | 6/1999 |

OTHER PUBLICATIONS

Keller, "Klinisch–chemische Labor–diagnotik für die Praxis", pp. 252–253, 1991, Germany—chemical names and formulas are in English language.

Sonntag, "Trockenchemie", Analytik mit tragergebundenen Reagenzien, pp. 296–297, 1988, Germany—chemical names and formulas are in English language.

Communication of a Notice of Opposition, European Patent Office, Sep. 8, 2003, with translation.

Summons to Attend Oral Proceedings Pursuant to Rule 71(1) EPC, European Patent Office, May 3, 2004.

Brief Communication, European Patent Office, Jul. 15, 2004, with translation.

Letter from Opposer to European Patent Office, European Patent Office, Sep. 23, 2004, with translation.

Grounds of Appeal, European Patent Office, Oct. 11, 2005, with translation.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 13 are cancelled.

Claims 2–3, 7–12, 14–15, 19–25, 27–30, and 32–34 are determined to be patentable as amended.

Claims 4–6, 16–18, 26 and 31, dependent on an amended claim, are determined to be patentable.

New claims 35–37 are added and determined to be patentable.

2. The article of claim [1] *9*, wherein said optical reading chamber does not extend completely through said base layer.

3. The article of claim [1] *9*, wherein said optical reading chamber contains at least one reagent with which the analyte in the sample reacts to form an optically detectable reaction product.

7. The article of claim [1] *9*, wherein said [second] opening *of said cover layer* communicates with a vent channel.

8. The article of claim [1] *9*, wherein said optical reading chamber is cylindrical in shape.

9. [The article of claim 1,] *An article for determining the presence or amount of analyte in a biological sample, said article comprising a multiple-layer element comprising:*

(a) *a base layer having two major surfaces, said base layer further having an opening, a flow channel, and an optical reading chamber, one end of which flow channel communicates with said opening in said base layer and the other end of which flow channel communicates with said optical reading chamber; and*

(b) *a cover layer in face-to-face contact with the major surface of said base layer containing said opening, said cover layer having an opening therein to vent said element;* wherein said optical reading chamber has a volume no greater than about 1 µL.

10. The article of claim [1] *9*, wherein said cover layer has a portion capable of transmitting light in register with said optical reading chamber.

11. The article of claim [1] *9*, wherein said base layer has a portion capable of transmitting light in register with said optical reading chamber.

12. The article of claim [1] *9*, wherein said [second] opening *of said cover layer* is not directly over said optical reading chamber.

14. The article of claim [13] *21*, wherein said optical reading chamber extends completely through said core layer.

15. The article of claim [13] *21*, wherein said optical reading chamber contains at least one reagent with which the analyte in the sample reacts to form an optically detectable reaction product.

19. The article of claim [13] *21*, wherein said [second] opening *of said cover layer* communicates with a vent channel.

20. The article of claim [13] *21*, wherein said optical reading chamber is cylindrical in shape.

21. [The article of claim 13,] *An article for determining the presence or amount of analyte in a biological sample, said article comprising a multiple-layer element comprising;*

(a) *a core layer having two major surfaces, said core layer further having an opening, a flow channel, and an optical reading chamber, one end of which flow channel communicates with said opening in said core layer and the other end of which flow channel communicates with said optical reading chamber; and*

(b) *a base layer in face-to-face contact with one major surface of said core layer; and*

(c) *a cover layer in face-to-face contact with the other major surface of said core layer, said cover layer having an opening therein to vent said element;* wherein said optical reading chamber has a volume no greater than about 1 µL.

22. The article of claim [13] *21*, wherein said cover layer has a portion capable of transmitting light in register with said optical reading chamber [is transparent].

23. The article of claim [13] *21*, wherein said base layer has a portion capable of transmitting light in register with said optical reading chamber.

24. The article of claim [13] *21*, wherein said [second] opening *of said cover layer* is not directly over said optical reading chamber.

25. A method for measuring the concentration of analyte in a sample comprising the steps of:

(a) obtaining a sample of biological fluid from the body of a patient;

(b) introducing the sample to the article of claim [1] *9*;

(c) allowing at least one reagent in the article to react with the analyte of interest in the sample; and (d) measuring the concentration of analyte in the sample by optical instrument.

27. The method *of* claim 25, wherein said at least one reagent comprises hexokinase.

28. The method *of* claim 25, wherein said at least one reagent comprises glucose dehydrogenase.

29. The method *of* claim 25, wherein said at least one reagent comprises diaphorase.

30. A method for measuring the concentration of analyte in a sample comprising the steps of:

(a) obtaining a sample of biological fluid from the body of a patient;

(b) introducing the sample to the article of claim [13] *21*;

(c) allowing at least one reagent in the article to react with the analyte of interest in the sample; and (d) measuring the concentration of analyte in the sample by optical instrument.

32. The method *of* claim 30, wherein said at least one reagent comprises hexokinase.

33. The method *of* claim 30, wherein said at least one reagent comprises glucose dehydrogenase.

34. The method *of* claim 30, wherein said at least one reagent comprises diaphorase.

*35. An article according to claim 9 wherein said opening in said base layer is formed through a lateral edge surface of said base layer.*

*36. An article according to any of claims 9 or 21 wherein said cover layer is a single layer of material with said opening in said cover layer comprising a hole formed through said material.*

*37. An article according to any of claims 9 or 21 wherein said flow channel has a narrower width than said optical reading chamber.*

* * * * *